(12) United States Patent
Lee et al.

(10) Patent No.: US 8,262,602 B2
(45) Date of Patent: Sep. 11, 2012

(54) REMOTE EXCHANGE PERITONEAL DIALYSIS

(75) Inventors: Patrick Lee, Long Grove, IL (US);
Annie Chiou, Mountain View, CA (US);
Meir Dahan, Lincolnwood, IL (US);
Bijan Elahi, Lake Forest, IL (US); Peter A. Hopping, Lutz, FL (US); Merrick F. Kossack, Arlington Heights, IL (US);
Joachim Prutsch, Chicago, IL (US)

(73) Assignees: Baxter International Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 531 days.

(21) Appl. No.: 12/131,755

(22) Filed: Jun. 2, 2008

(65) Prior Publication Data

US 2009/0299273 A1 Dec. 3, 2009

(51) Int. Cl.
*A61M 1/00* (2006.01)
(52) U.S. Cl. .......... 604/29; 604/179; 604/259; 604/262; 604/541
(58) Field of Classification Search .................... 604/28, 604/29, 541, 179, 259, 262; 206/438
See application file for complete search history.

(56) References Cited

U.S. PATENT DOCUMENTS

| | | | |
|---|---|---|---|
| 3,730,183 A | 5/1973 | Goldsmith et al. | |
| 3,783,866 A | 1/1974 | Tirkkonen | |
| 4,132,644 A | 1/1979 | Kolberg | |
| 4,178,240 A | 12/1979 | Pinkerton | |
| 4,190,047 A | 2/1980 | Jacobsen et al. | |
| 4,204,957 A | 5/1980 | Weickhardt | |
| 4,240,408 A | 12/1980 | Schael | |
| 4,301,879 A | 11/1981 | Dubow | |
| 4,318,447 A | 3/1982 | Northcutt | |
| 4,324,663 A | 4/1982 | Hirel et al. | |
| 4,367,859 A * | 1/1983 | Lamon ......................... | 248/318 |
| 4,372,846 A | 2/1983 | Yamagami et al. | |
| 4,412,917 A | 11/1983 | Ahjopalo | |
| 4,413,988 A | 11/1983 | Handt et al. | |

(Continued)

FOREIGN PATENT DOCUMENTS

EP 0824021 2/1998

(Continued)

OTHER PUBLICATIONS

European Search Report (PCT/US2009/045782) dated Sep. 30, 2009.

*Primary Examiner* — Bhisma Mehta
*Assistant Examiner* — Larry R Wilson
(74) *Attorney, Agent, or Firm* — K&L Gates LLP

(57) ABSTRACT

A portable, flexible peritoneal dialysis system is disclosed. The system includes a flexible harness, such as canvas or cloth, to mount a stiff housing with a heater for holding and heating fresh dialysis fluid. The harness includes straps or other suspending devices for holding a second, flexible housing for a drain bag for holding sent dialysis fluid. The upper portion of the system includes a hook and a load cell for suspending the remaining portions. The load cell is used to measure the weight of the apparatus. By keeping track of the weight and the changes, the quantity of fluid removed from the patient, spent dialysate, is tracked, as is fresh dialysate infused into the patient. An electronics or control portion controls heating of the fresh dialysate, and operation of pumps and valves for moving the dialysate. This portion also includes alarms and communications equipment.

17 Claims, 3 Drawing Sheets

U.S. PATENT DOCUMENTS

| | | | |
|---|---|---|---|
| 4,560,472 A | 12/1985 | Granzow et al. | |
| 4,582,598 A | 4/1986 | Bilstad et al. | |
| 4,585,436 A | 4/1986 | Davis et al. | |
| 4,586,920 A | 5/1986 | Peabody | |
| 4,606,826 A | 8/1986 | Sano et al. | |
| 4,629,015 A | 12/1986 | Fried et al. | |
| 4,661,246 A | 4/1987 | Ash | |
| 4,684,460 A | 8/1987 | Issautier | |
| 4,718,890 A | 1/1988 | Peabody | |
| 4,728,433 A | 3/1988 | Buck et al. | |
| 4,747,822 A | 5/1988 | Peabody | |
| 4,767,399 A | 8/1988 | Bollish | |
| 4,769,132 A | 9/1988 | Patono | |
| 4,844,810 A | 7/1989 | Richalley et al. | |
| 4,889,635 A | 12/1989 | Chevallet | |
| 4,923,598 A | 5/1990 | Schal | |
| 4,980,054 A | 12/1990 | Lavender | |
| 4,994,026 A | 2/1991 | Fecondini | |
| 5,004,459 A | 4/1991 | Peabody et al. | |
| 5,011,607 A | 4/1991 | Shinzato | |
| 5,141,492 A | 8/1992 | Dadson et al. | |
| 5,200,090 A | 4/1993 | Ford et al. | |
| 5,211,849 A | 5/1993 | Kitaevich et al. | |
| 5,247,434 A | 9/1993 | Peterson et al. | |
| 5,334,139 A | 8/1994 | Jeppsson et al. | |
| 5,344,568 A | 9/1994 | Kitaevich et al. | |
| 5,350,357 A * | 9/1994 | Kamen et al. | 604/29 |
| 5,445,610 A * | 8/1995 | Evert | 604/29 |
| 5,643,201 A | 7/1997 | Peabody et al. | |
| 5,722,947 A * | 3/1998 | Jeppsson et al. | 604/29 |
| 5,782,796 A | 7/1998 | Din et al. | |
| 5,928,177 A | 7/1999 | Brugger et al. | |
| 5,938,938 A | 8/1999 | Bosetto et al. | |
| 6,030,359 A * | 2/2000 | Nowosielski | 604/65 |
| 6,117,122 A | 9/2000 | Din et al. | |
| 6,327,895 B1 | 12/2001 | Jeppsson et al. | |
| 6,676,631 B1 | 1/2004 | Greter | |
| 7,033,539 B2 | 4/2006 | Krensky et al. | |
| 2004/0215129 A1 | 10/2004 | Edgson et al. | |
| 2004/0267183 A1 | 12/2004 | Chevallet | |
| 2007/0276328 A1 | 11/2007 | Childers et al. | |
| 2008/0093276 A1 | 4/2008 | Roger et al. | |
| 2008/0200867 A1 * | 8/2008 | Bedingfield | 604/29 |

FOREIGN PATENT DOCUMENTS

| | | |
|---|---|---|
| FR | 2371931 | 6/1978 |
| FR | 2397197 | 2/1979 |
| WO | 92/00768 | 1/1992 |
| WO | 93/06875 | 4/1993 |
| WO | 95/20985 | 8/1995 |
| WO | 9624396 | 8/1996 |

* cited by examiner

REMOTE EXCHANGE PERITONEAL DIALYSIS

BACKGROUND

This patent relates generally to medical fluid delivery systems and methods. More particularly, this patent discloses systems, methods and apparatuses for the control of fluid flow in kidney failure treatment systems.

Due to various causes, a person's renal system can fail. Renal failure produces several physiological impairments and difficulties. The balance of water, minerals and the excretion of daily metabolic load is no longer possible and toxic end products of nitrogen metabolism (urea, creatinine, uric acid, and others) can accumulate in blood and tissue.

Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life saving.

Hemodialysis and peritoneal dialysis are two types of dialysis therapies used commonly to treat loss of kidney function. A hemodialysis ("HD") treatment utilizes the patient's blood to remove waste, toxins and excess water from the patient. The patient is connected to a hemodialysis machine and the patient's blood is pumped through the machine. Catheters are inserted into the patient's veins and arteries so that blood can flow to and from the hemodialysis machine. The blood passes through a dialyzer of the machine, which removes waste, toxins and excess water from the blood. The cleaned blood is returned to the patient. A large amount of dialysate, for example about 120 liters, is consumed to dialyze the blood during a single hemodialysis therapy. Hemodialysis treatment lasts several hours and is generally performed in a treatment center about three or four times per week.

Another form of kidney failure treatment involving blood is hemofiltration ("HF"), which is an alternative renal replacement therapy that relies on a convective transport of toxins from the patient's blood. This therapy is accomplished by adding substitution or replacement fluid to the extracorporeal circuit during treatment (typically ten to ninety liters of such fluid). That substitution fluid and the fluid accumulated by the patient in between treatments is ultrafiltered over the course of the HF treatment, providing a convective transport mechanism that is particularly beneficial in removing middle and large molecules.

Hemodiafiltration ("HDF") is another blood treatment modality that combines convective and diffusive clearances. HDF uses dialysate to flow through a dialyzer, similar to standard hemodialysis, providing diffusive clearance. In addition, substitution solution is provided directly to the extracorporeal circuit, providing convective clearance.

Peritoneal dialysis uses a dialysis solution, also called dialysate, which is infused into a patient's peritoneal cavity via a catheter. The dialysate contacts the peritoneal membrane of the peritoneal cavity. Waste, toxins and excess water pass from the patient's bloodstream, through the peritoneal membrane and into the dialysate due to diffusion and osmosis, i.e., an osmotic gradient occurs across the membrane. The spent dialysate is drained from the patient, removing waste, toxins and excess water from the patient. This cycle is repeated.

There are various types of peritoneal dialysis therapies, including continuous ambulatory peritoneal dialysis ("CAPD"), automated peritoneal dialysis ("APD"), tidal flow APD and continuous flow peritoneal dialysis ("CFPD"). CAPD is a manual dialysis treatment. The patient manually connects an implanted catheter to a drain, allowing spent dialysate fluid to drain from the peritoneal cavity. The patient then connects the catheter to a bag of fresh dialysate, infusing fresh dialysate through the catheter and into the patient. The patient disconnects the catheter from the fresh dialysate bag and allows the dialysate to dwell within the peritoneal cavity, wherein the transfer of waste, toxins and excess water takes place. After a dwell period, the patient repeats the manual dialysis procedure, for example, four times per day, each treatment lasting about an hour. Manual peritoneal dialysis requires a significant amount of time and effort from the patient, leaving ample room for improvement.

Automated peritoneal dialysis ("APD") is similar to CAPD in that the dialysis treatment includes drain, fill, and dwell cycles. APD machines, however, perform the cycles automatically, typically while the patient sleeps. APD machines free patients from having to manually perform the treatment cycles and from having to transport supplies during the day. APD machines connect fluidly to an implanted catheter, to a source or bag of fresh dialysate and to a fluid drain. APD machines pump fresh dialysate from a dialysate source, through the catheter, into the patient's peritoneal cavity, and allow the dialysate to dwell within the cavity, and allow the transfer of waste, toxins and excess water to take place. The source can be multiple sterile dialysate solution bags.

APD machines pump spent dialysate from the peritoneal cavity, though the catheter, to the drain. As with the manual process, several drain, fill and dwell cycles occur during APD. A "last fill" occurs at the end of CAPD and APD, which remains in the peritoneal cavity of the patient until the next treatment.

Both CAPD and APD are batch type systems that send spent dialysis fluid to a drain. Tidal flow systems are modified batch systems. With tidal flow, instead of removing all of the fluid from the patient over a longer period of time, a portion of the fluid is removed and replaced after smaller increments of time.

Continuous flow, or CFPD, systems clean or regenerate spent dialysate instead of discarding it. The systems pump fluid into and out of the patient, through a loop. Dialysate flows into the peritoneal cavity through one catheter lumen and out another catheter lumen. The fluid exiting the patient passes through a reconstitution device that removes waste from the dialysate, e.g., via a urea removal column that employs urease to enzymatically convert urea into ammonia. The ammonia is then removed from the dialysate by adsorption prior to reintroduction of the dialysate into the peritoneal cavity. Additional sensors are employed to monitor the removal of ammonia. CFPD systems are typically more complicated than batch systems.

In each of the kidney failure treatment systems discussed above, it is important to control ultrafiltration, which is the process by which water (with electrolytes) moves across a membrane, such as a dialyzer or peritoneal membrane. For example, ultrafiltration in HD is a result of transmembrane and osmotic pressure differences between blood and dialysate across a dialyzer membrane. For a given osmotic pressure, the greater the transmembrane pressure the more rapid the ultrafiltration.

People with kidney failure typically retain water and fluids between treatments. That excess fluid needs to be removed during the next treatment. It is important to know how much fluid is removed so that the patient can be returned to their normal weight by the end of therapy. It is also important in some instances to know accurately the rate at which ultrafiltration is taking place at a given time during therapy.

Different systems have been employed to control ultrafiltration. One system described in U.S. Pat. No. 5,247,434 ("the '534 Patent"), assigned to the assignee of the present application, the entire contents of which are incorporated expressly herein by reference, controls ultrafiltration volumetrically. The patent describes a volumetrically balanced system that uses first and second chambers of substantially equal volume. Each chamber includes two compartments, one termed a "pre-dialyzer" compartment and the other a "post-dialyzer" compartment. Each opposing "pre" and "post" compartment of a chamber is separated by a flexible diaphragm. Solenoid-actuated valves control the filling and emptying of each compartment. In general, each compartment is completely filled before its contents are discharged. Also, the "pre" compartments are alternately filled and discharged and the "post" compartments are alternately filled and discharged. Filling a "pre" compartment causes a discharge of a corresponding and opposing "post" compartment, respectively. Filling a "post" compartment causes a discharge of a corresponding and opposing "post" compartment.

Since the volumes of opposing "pre" and "post" compartments of the two chambers are equal, the system volumetrically balances the flow of dialysate to and from the dialyzer. One benefit of this volumetrically controlled system is that dialysate flow to the dialyzer can be accurately measured over a wide range of flow rates.

The volumetric system works well for HD machines placed in centers, which produce dialysate online. In HD, the dialysate is not infused into the patient and is therefore not considered a drug. The balancing chambers can therefore be located inside the machine and sterilized between treatments. The same balancing chambers are used over and over.

PD infuses dialysate into the patient's peritoneum. Dialysate for PD is therefore considered a drug, and the dialysate must adhere to sterility requirements for a drug. Anything that comes in contact with the dialysate must also be sterilized and discarded after use. For PD then, at least a component of the balancing chambers would have to be sterilized and disposable, making balancing chambers for PD less attractive from a cost standpoint, compared for example to simple tubing used with peristaltic pumps.

Problems exist with prior fluid control systems employing scales to measure the weight of fluid delivered to and taken from the patient. For example, previous systems employing scales have had to be robust enough to accommodate the total size and weight of the dialysate used during treatment. The load cells of systems have an error associated with the process, based on a percentage of the total weight of fluid. As the total weight of the fluid increases, the error increases correspondingly and begins to compromise the accuracy of the system.

Also, because all the bags have to be weighed, a relatively robust mechanically-based hanging system has to be provided to handle the associated stresses. In addition, the size of the weighing system makes it more prone to interferences from bumps or hits for example. The size of the weighing system can also make storage of the multiple bags difficult, for example, providing a container or support system capable of isolating the weighing system from mechanical interferences and protecting the load cell.

Moreover, multiple supply bags can be complex and difficult for the patient to attach to the weighing system. For example, the multiple bags may have to be lifted to an inconvenient height. Also, in prior gravimetric systems, spent dialysate has to be collected, requiring the operator to carry heavy, full bags of fluid twice, once for setup and again after treatment. Finally, previous systems purporting to meet these needs have not been portable, i.e., they tend to be relatively bulky. See, e.g., U.S. patent application Ser. No. 11/420,608, U.S. Pat. No. 8,226,595, and U.S. patent application Ser. No. 11/422,267. A need therefore exists for a simplified and relatively inexpensive fluid control system for kidney failure treatments, especially for peritoneal dialysis treatment, which is accurate and easy to maintain.

SUMMARY

One embodiment is a peritoneal dialysis system. The system includes a flexible mounting apparatus, a first housing for a first container for fresh dialysis fluid mounted on the flexible mounting apparatus, an electronics bay with a controller mounted on the first housing, a flexible housing for a second container for spent dialysis fluid mounted on the flexible mounting apparatus at a lower height than the first housing, a mount for holding the flexible mounting apparatus, and a mass sensor between the mount and the flexible mounting apparatus. In this embodiment, the dialysis fluid is heated before being placed into the housing.

Another embodiment is a peritoneal dialysis system. The system includes a flexible mounting apparatus, a stiff housing with a heater for a first container for fresh dialysis fluid, the stiff housing mounted to the flexible mounting apparatus, an electronics bay with a controller mounted on the stiff housing, a conformable housing for a second container for spent dialysis fluid, the conformable housing suspended by the flexible mounting apparatus below the stiff housing, a vacuum pump in operable communication with the controller, a mount for holding the flexible mounting apparatus, and a load cell between the mount and the flexible mounting apparatus.

Another embodiment is a for performing peritoneal dialysis. The method includes steps of mounting a dialysate drain bag of a portable, flexible peritoneal dialysis system in a first housing at a height lower than a peritoneum of a patient, and mounting a dialysate fill bag of the portable, flexible peritoneal dialysis system in a second flexible, deformable housing at a height higher than the peritoneum of the patient, wherein the flexible peritoneal dialysis system includes the first and second housings and wherein the first housing and second housing are mounted within the flexible peritoneal dialysis system with freedom to move with respect to one another. The method also includes steps of heating the dialysate fill bag with a heater of the portable, flexible peritoneal dialysis system until a desired temperature is achieved, draining spent dialysate into the drain bag using a pump or a vacuum until a desired mass of spent dialysate is achieved, and filling the peritoneum with fresh dialysate using gravity or a pump until a desired mass of dialysate fill is achieved. A roller pump or vacuum chamber may be used to drain the spent dialysate.

Additional features and advantages are described herein, and will be apparent from the following Detailed Description and the figures.

DETAILED DESCRIPTION

Embodiments of a portable, flexible peritoneal dialysis system are desirably lightweight, sturdy, and durable. Of course, the new system must meet all the requirements of a standard peritoneal dialysis system and must be able to withstand years of use by patients and their caregivers or helpers. For example, fresh dialysis fluid is heated to about 37° C., body temperature, to avoid shocking elderly, frail patients. This is desirably accomplished in the new system, and thus a pan or container for fresh dialysate includes a relatively rigid or stiff container for a fresh dialysate bag. The container or housing is also desirably made of a material suitable for warming the fresh dialysate fluid. Containers may be metal or plastic, and as mentioned, they should be relatively stiff or rigid so that if they contain integral heating elements, there is no rubbing or fretting of the heating elements when bags are moved, adjusted, changed, and so forth. Other embodiments may include non-integral heaters, such as an in-line heater or a separate radiant-heat heater between the housing and the dialysis bag. As noted, the container itself may have thermal elements embedded within the container.

Figure 1:
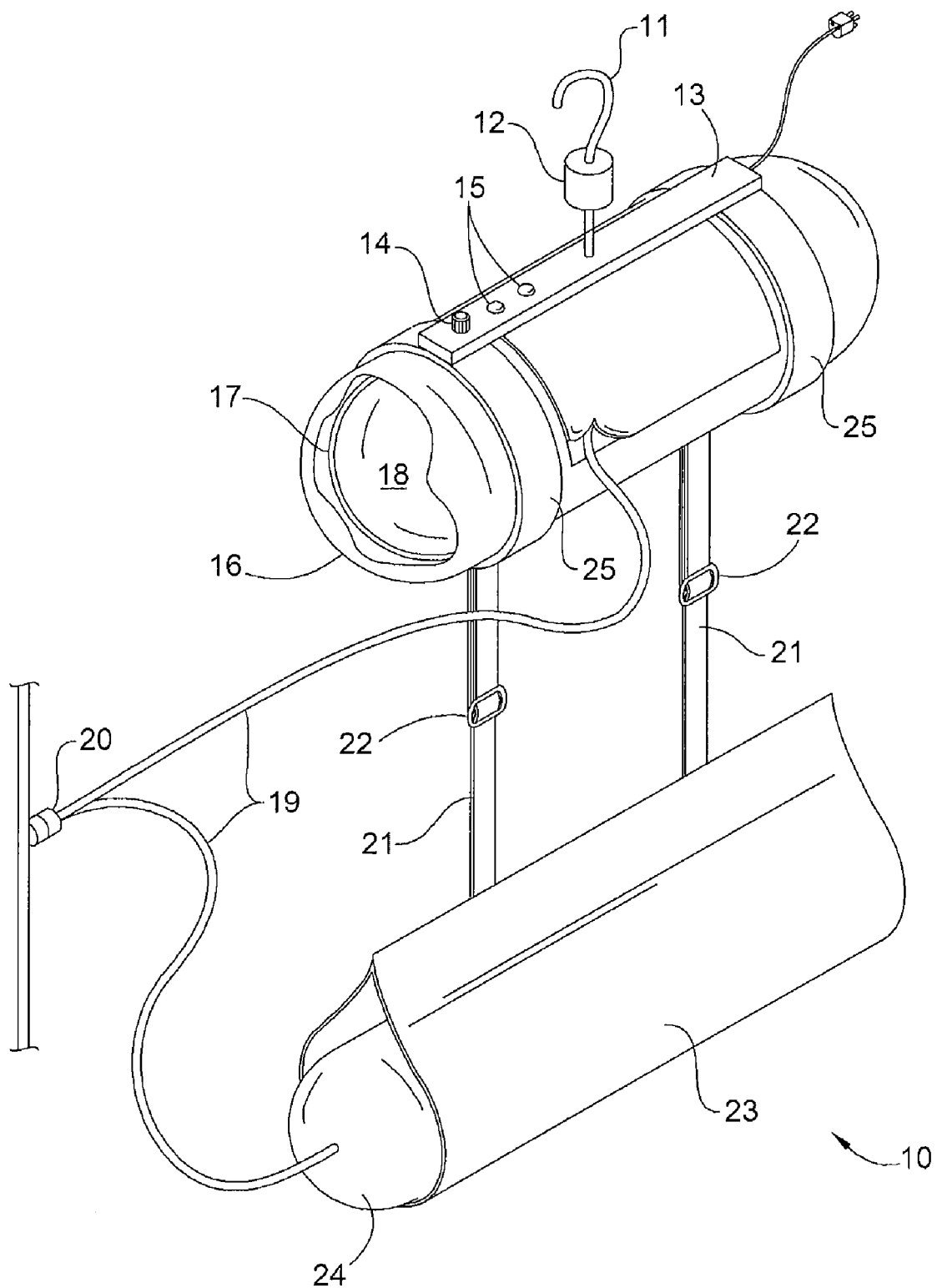
FIG. 1 depicts an isometric overview of an embodiment.

One embodiment of a flexible, portable peritoneal dialysis system is depicted in FIG. 1. The flexible peritoneal dialysis system 10 includes a hook 11 for suspending the system from overhead. The hook may be hooked over a beam, through an orifice in a beam, or hooked through an eye-bolt or another hook suspended overhead and capable of supporting the system. The mass of the dialysate fluid is the greatest mass within the system. A 2.5 L bag of dialysate weighs about 2.5 kg (about 8 lbs). Even with two 2.5 L containers of fresh dialysate and a 2.5 L bag of spent dialysate, the total mass should be about 7.5 kg, with and extra 15 kg for the dialysis system, a total of about 22.5 kg (about 50 lbs). With a good safety margin, the hook should be able to support about 40 kg or about 90 lbs. This safety margin will also accommodate patients using a 3.5 L dialysate container.

An important part of the system is the load cell 12 that measures and reports the mass suspended. As shown in FIG. 1, load cell 12 may be used to support the peritoneal dialysis system. Tension-measuring load cells are available from a number of companies, such as Futek Advanced Sensor Technology, Irvine, Calif., U.S.A. Model LCB200 is an example. Such sensors are also available from Omega Engineering Co., Stamford, Conn., U.S.A. Model L101-25 is an example. In other embodiments, the dialysis system may be supported from underneath and a compression-type load cell used. In yet other embodiments, separate load cells may be used for measuring the mass within the fresh dialysate housing and the spent dialysate housing. The measured mass or masses are reported to a system controller, described below, and the system operated when the desired mass or masses are achieved. Instead of a load cell, a strain gage or other sensor for sensing mass may be used.

In FIG. 1, the next element is an electronics or control portion 13, which may be housed as shown, atop the fresh dialysis fluid housing 16, or may be located elsewhere on the structure, as desired. Fluid housing 16 in the embodiment of FIG. 1 is flexible, similar to a canvas bag. In other embodiments, the housing may be made of more stiff material, such as stiffer plastic or more rigid aluminum. The electronics portion 13 is further explained in the embodiment of FIG. 2. This is the portion that operates the dialysis system, and typically includes a computer microcontroller and a temperature controller. The control portion accepts inputs from an operator, such as a patient or a caregiver. The control portion also receives other inputs, such as an input from the temperature control knob 14, the load cell reading, the temperature of the fresh dialysate, the time elapsed since the beginning of the therapy session, and so forth. The control section 13 also has output components, such as LED lamps 15 for signaling. Other outputs are discussed below.

The upper housing 16, flexible in the embodiment shown in FIG. 1, is meant to enclose a container 18 of dialysis fluid. The upper housing 16 may be roughly in the shape of a cylinder as shown, or may be in the shape of a flat rectangular pan with side walls a few inches or cm high (about 3 inches, 7-8 cm), to securely hold a multi-liter bag or container of dialysis fluid. Housing 16 in this embodiment completely contains and encloses container 18 and retains the heat from heater 17 used to warm the dialysis fluid to body temperature. As mentioned above, the heater may be any suitable type of heater, such as an electrical resistance heating pad in the bottom of the housing, warming the dialysis fluid. Other embodiments may use an inline or other type of heater, but a standard "heating-pad" type of flexible conduction heater is simple and reliable. In one embodiment, housing 16 is about 270 mm long (about the length of the container), and its cross section, in the form of a flattened ellipse as shown in FIG. 1, is about 120 mm wide, and about 180 mm high.

In another embodiment, the housing 16 or chamber is airtight and is sufficiently stiff to withstand the application of pressure, such as air pressure, to pump dialysate fluid from the housing or from a container within the housing to the patient. The housing should also sufficiently stiff to withstand the application of vacuum when the dialysate fluid is being removed from a patient by applying vacuum to the chamber or to a container within the chamber, to void the dialysate from the patient, in applications using only a single bag. The airtight housing or clamshell is sufficiently airtight to withstand reasonable pressure or vacuum in order to pump dialysis fluid.

The system also includes a second housing 23 for holding a dialysis drain bag 24. The drain bag is used to contain spent dialysis fluid that is evacuated or pumped from the patient after a retention period. There is no need for a housing that holds its shape for the drain bag, so a flexible, deformable material may be used. Examples are cloth, tent, or canvas material. The only requirement is the ability to hold the drain bag. If canvas or a similar material is used, this portion becomes very light in weight, as well as being flexible and portable. Second housing 23 is suspended from first housing 16 by adjustable canvas or nylon straps 21, the adjustability provided by buckles that allow the user to select the length of the straps 21. The straps 21 may have extensions 25 that encircle housing 16, forming a flexible mounting apparatus with straps 21 that holds both housings 16, 23. Alternatively, straps 21 may loop around clips (not shown) on the bottom surface of housing 16. In this embodiment, the flexible mounting apparatus includes straps 21, which allow translation and rotation with respect to housings 16 and 23.

Because the housings 16, 23 are connected by straps 21, the housings, even when containing dialysate containers, may be moved with respect to one another. That is, lower housing 23 may be moved up or down, backwards or forwards, i.e., translated or rotated with respect to the upper housing 16, albeit possibly with some twisting of the straps. It will be recognized by those having skill in the art that the height of the upper housing may be adjusted by lengthening a straight portion of hook 11 or by inserting a rod or other connector between the load cell 12 and the electronics housing portion 13. Alternatively, the straps 25 may be lengthened so that housing 16 settles into a lower height than depicted in FIG. 1. In this embodiment, straps 25 are suspended from electronics portion 13, which is supported by load cell 12, which is suspended from hook 11.

In one embodiment, as shown in FIG. 1, housing 23 is about 440 mm long and also has a shape of a flattened ellipse, about 270 mm high with a diameter of about 160 mm. The system may also include tubing 19 or other plumbing connections to a Y-connector 20 that connects to peritoneal access for the patient. The valves and other devices, such as pumps, used to move the dialysis fluid are explained below with reference to FIGS. 2-3.

The system works by placing a known charge of peritoneal dialysis fluid, such as a known mass or volume, within the peritoneum of the patient, and then removing the charge after a period of time, such as several hours later. The dialysis fluid within the peritoneum then extracts an amount of ultrafiltrate from the patient. Thus, the volume or weight of spent dialysis fluid normally exceeds the amount that was input to the patient. The weight or volume gain for a particular patient is relatively stable and is used to calculate an expected volume or weight of spent fluid to be removed from the patient. The control unit calculates the drain and fill volumes by subtracting the pre- and post-pumping weights for both the drain and fill cycles. The expected amount is used as an input to a drain logic algorithm that optimizes fluid removal for the patient. For example, the expected amount can be used as a minimum to establish alert limits for the patient, e.g., a light or an audio alarm, that their typical drain has or has not been reached. The load cell and a computer within the system, along with valves and pumps, are used to control the process. Alternatively, a computer at the hospital or clinic may be used to calculate the desired pre- and post-weights, using radio or land line communications capabilities within the system described below.

In another embodiment, the system has an air-tight housing or chamber (clamshell) with a vacuum pump and valves, for pumping dialysate fluid to fill and drain the patient. This may be achieved by using a cassette and manifold for valving and routing the vacuum and the dialysate fluid; alternatively, line clamps under machine control may be used. In another embodiment, instead of a cassette, the fill and drain containers may be contained within the air-tight chamber. To fill the patient, pressure is applied to the chamber; to drain the patient, vacuum is applied to the chamber. Pressurized air may be obtained from a small compressor, a small pneumatic pump, or other suitable device.

Figure 2:
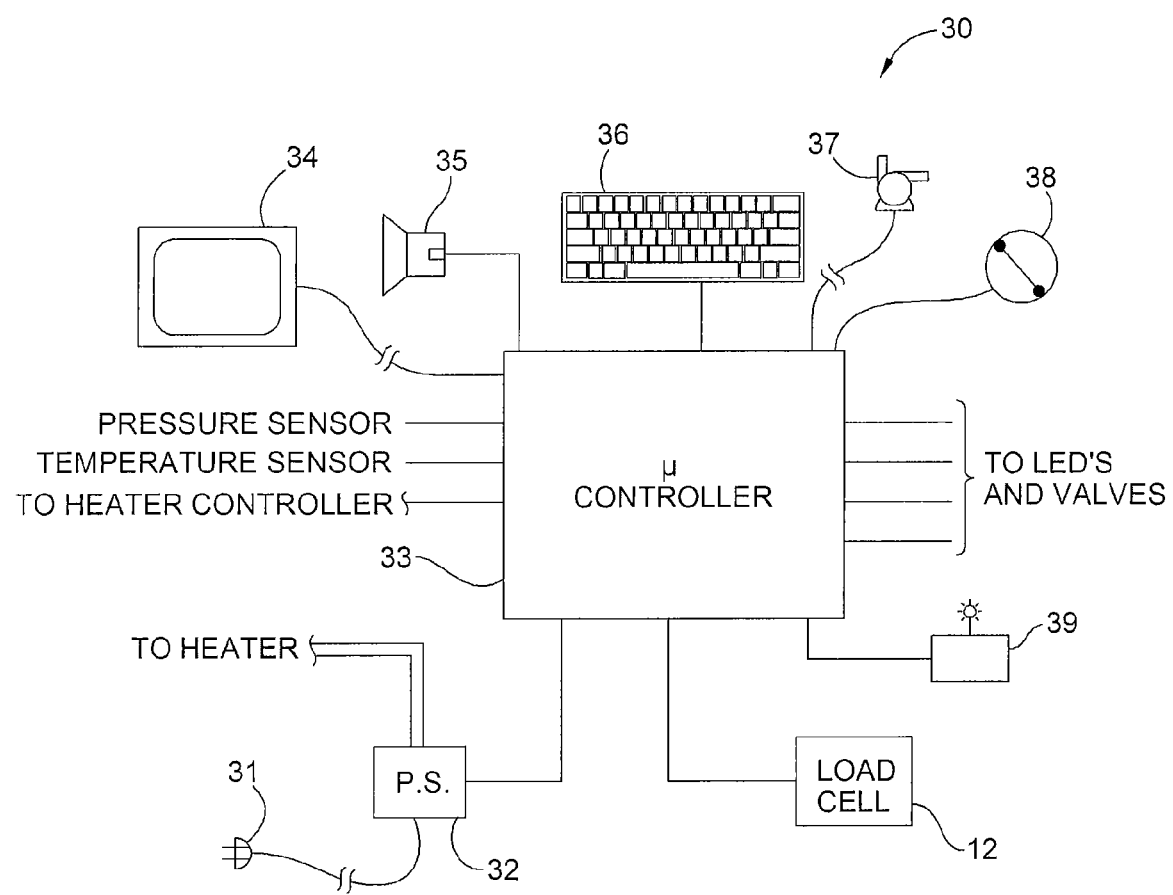
FIG. 2 is a schematic view of a control system.
Figure 3:
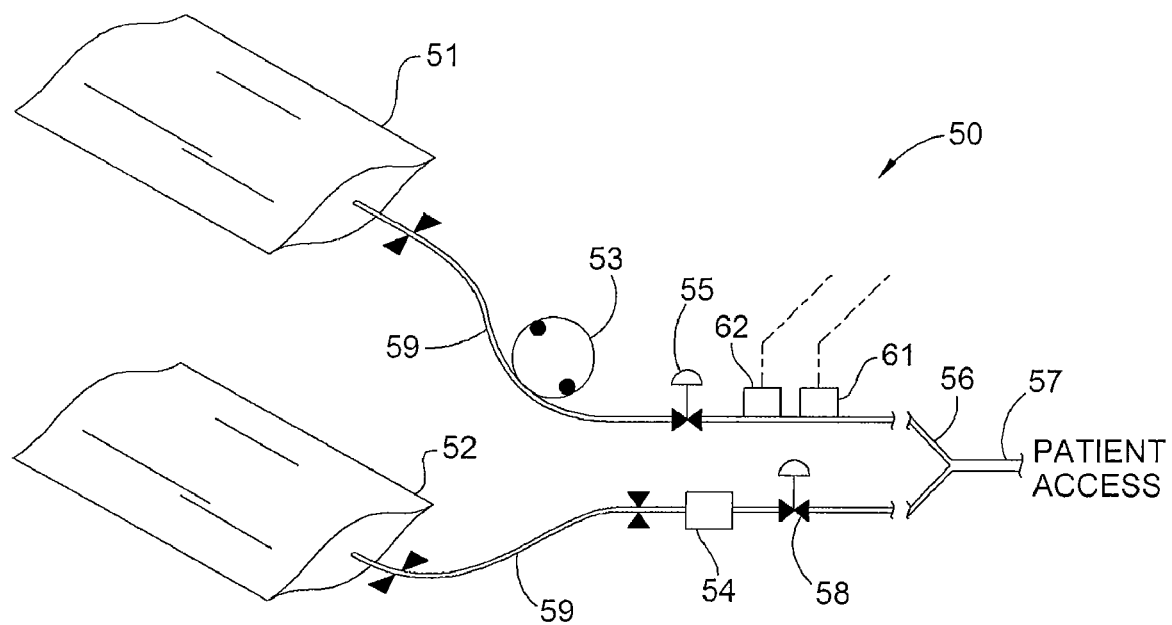
FIG. 3 is an embodiment of valving and connection for an embodiment.

FIG. 2 depicts a control system 30 for the flexible, portable peritoneal dialysis system. The control system receives conventional electrical power from a power cord 31 that is suitable from normal household, clinic, or hospital AC power. The principal user of power in this system is the heater. Thus, the input power is sent to a power supply 32 for conversion into the particular power needed for the heater, as shown. The power supply also produces 5 VDC power for the system microcontroller 33 and the other components of the system as needed, such as for the LED lamps. Other voltages may be produced by the power supply 32 as needed for each component of the system. The microcontroller receives a number of inputs from system components, such as a temperature selector 14 (see FIG. 1), and, if used, an input and output to a separate heater controller. The microcontroller may itself include a routine for controlling the heater rather than using a separate heater controller. A temperature sensing element, or temperature sensor, such as a thermocouple or thermistor, is used to measure the temperature of the dialysis fluid and to control the heating of the dialysis fluid. A pressure sensor may also be placed at one or more points within the system to gauge pressure of fluid to and from the patient. In particular, a vacuum gauge, or absolute pressure gage, may be placed on the drain line to avoid using too much suction on the drain line, which could irritate the peritoneum of the patient.

The control system 30 also accepts inputs from the load cell 12 and from a keypad 36, or optionally, a keyboard. The control system 30 includes a number of outputs also. A monitor 34, such as a video screen or a digital read-out, may be used to output the temperature of the dialysate, the time elapsed, and so forth. Other outputs include signals to vacuum pump 37 or dialysate pump 38, which may be a peristaltic pump or other desired pump. The system also includes signal processing circuitry and a radio 39 for wireless transmission of desired therapy information to a hospital or clinic central computer. The signal processing circuitry and wireless transmitter are small and compact, and are easily placed within the control portion.

One module that works is a wireless module in accord with ZigBee/IEEE 805.15.4. This is a standard for a very low power radio system with a very limited range, about 10-20 feet. Modules made in accordance with this standard may be purchased from Maxstream, Inc., Lindon, Utah, U.S.A., Helicomm, Inc., Carlsbad, Calif., U.S.A., and ANT, Cochrane, Alberta, Canada. The module is very small, and may be about 2 cm square (about 1 inch square), and about 3 mm thick (⅛ inch). The signal processing circuitry formats the digital data and routes it to a data buffer before transmission to a remote site. Other equipment in accord with other specifications may be used instead, such as IEEE 802.15.1 ("Bluetooth"). Alternatively, the microprocessor may report desired therapy information via a landline, such as a wire harness connected to the appropriate site for receiving the information, such as a communications center of a hospital or clinic.

The system may sound an alarm if therapy parameters are exceeded through speaker 35 or by illuminating one or more LEDs 15. An alarm may also be given through the monitor 34 in conjunction with stopping the therapy session. The controller may use the outputs by sending a signal to the appropriate output when the temperature of the warmed dialysate fluid is too high or too low, when the therapy session has taken too long, or when any other required parameter is exceeded.

The peritoneal dialysis system described above and the control system also described are used to carry out a peritoneal dialysis therapy for a patient. Most of the dialysis fluid equipment 50 presented in FIG. 3 has already been mentioned. In one embodiment, the equipment includes a container 51 of fresh dialysis fluid, such as a 2.5 L bag of Dianeal® PD-2 solution, Baxter International, Inc., Deerfield, Ill., U.S.A. The container may include tubing 59 and a Y-connector 56, to connect to a patient access device 57, such as an implanted catheter.

A pump 53, such as a peristaltic pump, is used to pump the solution into the peritoneal cavity of the patient. A valve 55 or a line clamp may be used as shown between the container and the Y-connector 56. Alternatively, gravity may be used to flow the solution, the flow rate determined by the vertical distance or height difference between the container 51 and the patient's peritoneum. The flow rate is also determined by the setting on valve 55 or other restriction in the tubing 59 between container 51 and Y-connector 56. When the solution has been pumped into the patient, the mass of the emptied system, as seen in FIG. 1, is noted. Alternatively, the system may include a scale or load cell under container 51 to note the difference. As noted above, a pressure sensor 61 and a temperature sensor 62 may be used at desired points on the tubing or near the pumps 53, 54 to provide feedback to the system controller and to operate the remote exchange system.

After a prescribed dwell period, the dialysis within the patient is removed. Drain bag 52 is connected to the Y-connector 56 by tubing 59 and by a valve 58 or a line clamp. Pump 54, shown schematically, may be a vacuum pump or may instead be a conventional liquid pump. The vacuum pump may be used as a pump, or alternatively may be used to start siphoning from the patient, with the drain container 52 at a height lower than the peritoneum of the patient. As noted, pump 54 may be a conventional liquid pump, such as a diaphragm pump or a peristaltic pump. The number of strokes or revolutions may be noted to track the volume of dialysate removed. However, the load cell for the peritoneal dialysis system will note the change in mass as the drain bag is filled. When the desired weight change has been achieved, the flow, the pump or the siphon may be stopped. Extra running of the pump when the spent dialysis fluid has been largely removed can cause irritation or damage to the lining of the patient's peritoneum.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

What is claimed is:

1. A peritoneal dialysis system, comprising:
   a flexible mounting apparatus;
   a first housing for a first container for fresh dialysis fluid mounted on the flexible mounting apparatus;
   an electronics bay with a controller mounted on the first housing;
   a flexible housing for a second container for spent dialysis fluid mounted on the flexible mounting apparatus and suspended from the first housing at a lower height than the first housing by at least one adjustable strap, the adjustable strap having an extension that surrounds the first housing;
   a mount for holding the flexible mounting apparatus; and
   a mass sensor between the mount and the flexible mounting apparatus.

2. The peritoneal dialysis system of claim 1, wherein the first housing further comprises a heater.

3. The peritoneal dialysis system of claim 1, further comprising a vacuum pump controlled by the controller.

4. The peritoneal dialysis system of claim 1, further comprising a wireless communication module connected to the controller.

5. The peritoneal dialysis system of claim 1, further comprising a visual or audio alarm connected to the controller.

6. The peritoneal dialysis system of claim 1, wherein the flexible housing comprises a canvas or cloth harness suspended by straps from the first housing.

7. The peritoneal dialysis system of claim 1, wherein the mount comprises a hook for suspending the flexible mounting apparatus.

8. The peritoneal dialysis system of claim 1, wherein the at least one adjustable strap is formed from a material selected from the group consisting of cloth, tent, canvas, nylon, and combinations thereof.

9. A peritoneal dialysis system, comprising:
   a flexible mounting apparatus;
   a stiff housing with a heater for a first container for fresh dialysis fluid, the stiff housing mounted to the flexible mounting apparatus;
   an electronics bay with a controller mounted on the stiff housing;
   a conformable housing for a second container for spent dialysis fluid, the conformable housing suspended by the stiff housing below the stiff housing by at least one adjustable strap, the adjustable strap having an extension that surrounds the stiff housing;
   a vacuum pump in operable communication with the controller;
   a mount for holding the flexible mounting apparatus; and
   a load cell between the mount and the flexible mounting apparatus.

10. The peritoneal dialysis system of claim 9, wherein a height of the conformable housing is adjustable by the strap suspending the conformable housing.

11. The peritoneal dialysis system of claim 9, wherein the stiff housing is airtight and is capable of holding a vacuum or a pressure for pumping dialysis fluid.

12. The peritoneal dialysis system of claim 9, wherein a height of the flexible mounting apparatus is adjustable.

13. The peritoneal dialysis system of claim 9, wherein a height of the flexible mounting apparatus is adjustable by adjusting the mount and the load cell.

14. The peritoneal dialysis system of claim 9, further comprising interconnecting lines and a Y-connector for connecting to an access device of a patient.

15. The peritoneal dialysis system of claim 9, further comprising valves for controlling flow of fresh dialysis fluid from the first container to the patient and flow of spent dialysis fluid from the patient to the second container.

16. The peritoneal dialysis system of claim 9, further comprising a pump for pumping dialysis fluid.

17. The peritoneal dialysis system of claim 9, wherein the at least one adjustable strap is formed from a material selected from the group consisting of cloth, tent, canvas, nylon, and combinations thereof.

* * * * *